United States Patent
Crozafon et al.

(10) Patent No.: US 6,272,930 B1
(45) Date of Patent: Aug. 14, 2001

(54) TUBE ASSEMBLY INCLUDING A PRESSURE MEASURING DEVICE

(75) Inventors: Philippe Crozafon, Nice; Gilles Bos, La Balme de Sillingy; Angel Ortuno, Choisy, all of (FR)

(73) Assignee: Corneal Industrie, Pringy (FR)

(*) Notice: Subject to any disclaimer, the term of this patent is extended or adjusted under 35 U.S.C. 154(b) by 0 days.

(21) Appl. No.: 09/180,517

(22) PCT Filed: May 12, 1997

(86) PCT No.: PCT/FR97/00834

§ 371 Date: Nov. 9, 1998

§ 102(e) Date: Nov. 9, 1998

(87) PCT Pub. No.: WO97/43615

PCT Pub. Date: Nov. 20, 1997

(30) Foreign Application Priority Data

May 10, 1996 (FR) .................................................. 95 05872

(51) Int. Cl.[7] ........................................................ G01L 7/10
(52) U.S. Cl. ............................................................ 73/729.2
(58) Field of Search .............................. 73/714, 715, 716, 73/717, 720, 721, 726, 727, 756, 729.2, 730

(56) References Cited

U.S. PATENT DOCUMENTS 3,863,504    2/1975  Borsanyi .
5,581,038 *  12/1996 Lampropoulos et al. ............. 73/756
5,605,360 *   2/1997 Kurisaki et al. ....................... 73/756

FOREIGN PATENT DOCUMENTS

| 0 092 827  | 5/1984 | (EP) . |
| 59-012254  | 1/1984 | (JP) . |
| 7-155857   | 6/1995 | (JP) . |
| 7-198521   | 8/1995 | (JP) . |

* cited by examiner

Primary Examiner—William Oen
(74) Attorney, Agent, or Firm—Wolf, Greenfield & Sacks, P.C.

(57) ABSTRACT

The invention relates to a device for measuring the pressure of a liquid flowing in a tube (20, 22) into or out from the human body, the device comprising: an elongate body (10) having first and second ends (12, 14), an axial bore (16) opening out into said ends and defined by an inside wall (16a), and a recess (18) opening out into said axial bore between its two ends, each end of said body having means (12a, 14a) for connection to said tube (20, 22); and a pressure sensor (30) having a portion mounted in sealed manner in said recess (18), the surface of said sensor which is subjected to the pressure of said liquid being of a shape that is flush with the inside wall of said axial bore at said recess.

12 Claims, 2 Drawing Sheets

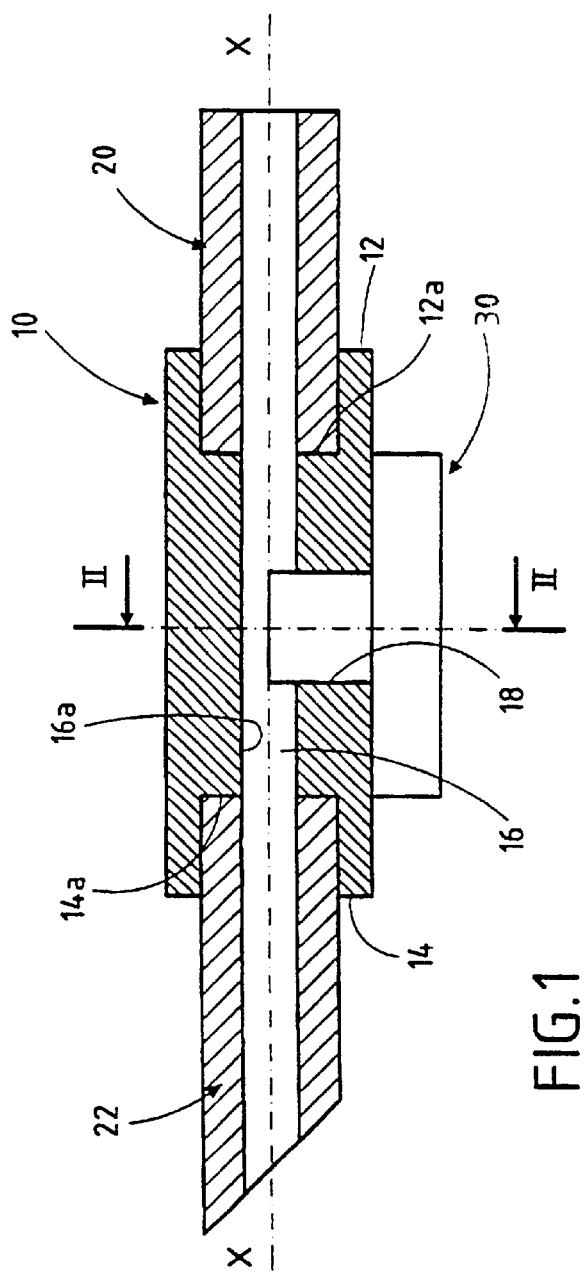
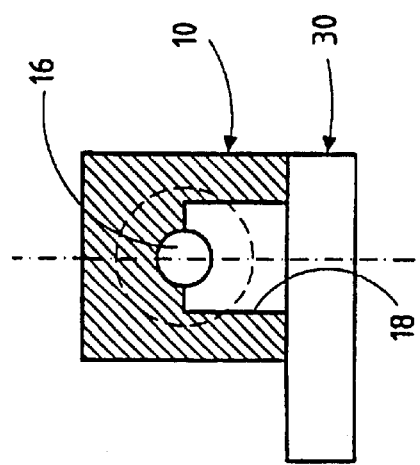
FIG.1
FIG.2

TUBE ASSEMBLY INCLUDING A PRESSURE MEASURING DEVICE

The present invention relates to a device for measuring the pressure of a liquid flowing in a tube and extracted from the human body.

More precisely, the invention relates to a device that makes it possible continuously to measure the pressure of a liquid flowing in a tube connected to a portion of the human body, said tube serving to extract the liquid from the human body, the pressure then naturally being negative relative to atmospheric pressure, suction also being provided by means of a pump.

Such a problem arises particularly, but naturally not exclusively, when implementing the so-called "phaco-emulsification" technique. That technique relates to surgery of the eye and consists in removing the lens by breaking it up by means of an ultrasound emitter. The lens fragments obtained in this way are extracted from the eye via a cannula, and more precisely they are extracted from the capsular bag which contains the lens. This extraction is performed by means of a tube connected to an extractor pump, thus making it possible to extract the lens fragments that are immersed in a liquid which is of the physiological serum type. Simultaneously, another cannula is naturally used to inject synthetic physiological liquid into the eye and more precisely into the capsular bag, in order to replace at least temporarily the lens material that has been extracted, said injection generally being performed merely under the effect of gravity.

In that type of operation, it is extremely important for the lens region to contain at all times a volume of liquid and solid material that is substantially constant so as to keep the shape of the anterior chamber substantially constant. Otherwise, in particular in the event of a large and sudden decrease in volume, there could be major and irreversible damage to the eye and in particular to the retina by the retina becoming detached, due to a sudden drop in the pressure to which it is subjected by the vitreous humor.

Unfortunately, in the phaco-emulsification operation, and more precisely while sucking out the lens fragments, such sudden pressure variations can indeed occur, for example when a lens fragment temporarily blocks the extractor cannula. Under such circumstances, when the lens fragment ceases to block the cannula, because of the suction that is established in the tube, liquid is sucked out at a very high rate that is not compensated by the inflow of the replacement liquid.

It should also be recalled that because of the extraction that is taking place, the "normal" pressure of the liquid is lower than atmospheric pressure. Under normal operating conditions, the pressure drop relative to atmospheric pressure is of the order of 50 mm to 500 mm of mercury, and more usually lies in the range 150 mm to 350 mm of mercury.

Under such circumstances, as in other applications, it is important to be able to monitor the pressure that actually obtains in the tube, whether the tube is a suction tube or an injection tube, and to do so continuously, accurately, reliably, and with a time constant that is very short.

Unfortunately, in particular in phaco-emulsification techniques, pressure in the tube is monitored via a duct element branching off from the main tube and connected to a pressure sensor. This branch tube is filled with air in order to protect the sensitive membrane of the sensor from the damage it might suffer from coming into contact with the liquid flowing in the tube. If there is a sudden change of pressure, the air held captive in the branch tube is naturally far more compressible than the liquid flowing in the main tube, and this can give rise firstly to significant error in the pressure value as measured, and above all it can give rise to a significant delay between pressure varying in the tube and that variation being detected by the pressure sensor. As explained above, such measurement errors can lead to very damaging consequences during an operation, in particular when performing phaco-emulsification.

An object of the present invention is to remedy that drawback by providing a pressure measuring device which can be fitted to a tube that is being used to suck a liquid from the human body, the device making it possible at all times to measure the actual pressure of the liquid flowing in the tube with great accuracy and with a very short time constant.

According to the invention, this object is achieved by a device for measuring the pressure of liquid flowing in a tube for causing a liquid to flow out from the human body, which device is characterized in that it comprises:

duct means having an axial bore whose wall has an inside face that is substantially flush with the tube, said means including an orifice passing through the wall and opening out in the inside face, a first end connected to a first portion of said tube and a second end connected to a second portion of the tube; and a pressure sensor for measuring the pressure of said liquid in the tube, said sensor having a surface which is subjected to the pressure of said liquid, at least a portion of said sensor being mounted in sealed manner in said orifice, in such a manner that said sensitive surface is substantially flush with the inside face of the wall of the duct means.

In a preferred embodiment of the invention, the device comprises:

an elongate body having first and second ends and with an axial bore formed therein, the bore opening out into said first and second ends and being defined by an inside wall, each end having means for connection to said tube, said body also having a recess that opens out into said axial bore between its first and second ends; and a pressure sensor mounted in said recess, said sensor having a surface which is subjected to said pressure and whose shape is substantially flush with the inside wall of the bore at said recess.

It will be understood that because of this integrated disposition of the pressure sensor, the face of the sensor which is subjected to said pressure is substantially flush with the tube element defined by the body of the pressure measuring device. This avoids any accidental accumulation of air or any other gas which could cause disturbances in the speed and the magnitude of the measurement of the pressure that actually obtains in the tube.

In the present text, the term "substantially flush" means that the pressure sensitive surface of the sensor is not strictly speaking a portion of the corresponding surface of the inside wall of the duct means, but that relative to the corresponding surface of the inside wall said pressure sensitive surface leaves an empty volume that is very small. This volume is preferably less than 10 mm$^3$, and more preferably less than 5 mm$^3$.

Other characteristics and advantages of the invention appear better on reading the following description of an embodiment of the invention given by way of non-limiting example.

The description refers to the accompanying figures, in which:

FIG. 1 is a longitudinal section of a first embodiment of the pressure measurement device, shown in full;

FIG. 2 is a section view on line II—II of FIG. 1;

Figure 3:
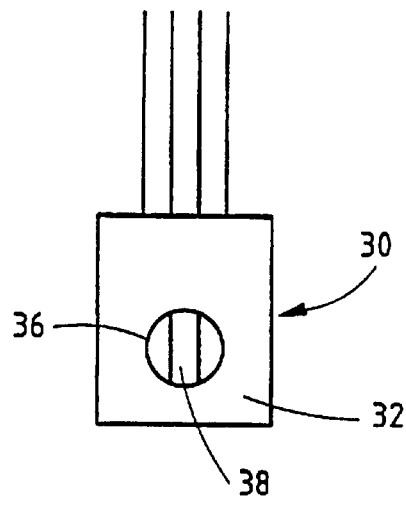
FIG. 3 is a face view of the pressure sensor proper.

The pressure measurement device as a whole is described initially with reference to FIGS. 1 and 2. In a preferred embodiment, the device is essentially constituted by a body 10 of elongate shape having two ends 12 and 14. In the body 10 there is provided an axial bore 16 which is preferably cylindrical in shape, said axial bore 16 opening out into the ends 12 and 14 of the body 10. By way of example, the body 10 is rectangular in right cross-section. The body 10 is also provided with a recess 18 whose main direction extends orthogonally to the axis XX' of the axial bore 16. The recess 18 opens out into the axial bore 16.

The ends 12 and 14 of the body 10 of the device preferably include respective setback portions 12a and 14a enabling the body 10 to be connected in sealed manner to an upstream tube portion 20 and to a downstream tube portion 22, which tube carries a flow of the liquid that is to be extracted from a part of the human body, in particular from the eye if the pressure measurement device is being used during a phaco-emulsification operation. One of the tube portions is connected to a suction pump and the other portion is connected to a cannula.

The body 10 of the device is preferably made by molding a rigid biocompatible plastics material, such as PMMA or any other analogous material.

The pressure measurement device also comprises a differential pressure sensor 30 which is mounted on the body 10 and which includes, as explained below, an extension which penetrates into the recess 18.

Figure 4:
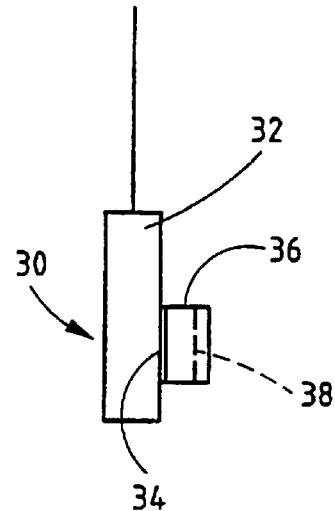
FIG. 4 is a side view of the pressure sensor shown in FIG. 3.
Figure 5:
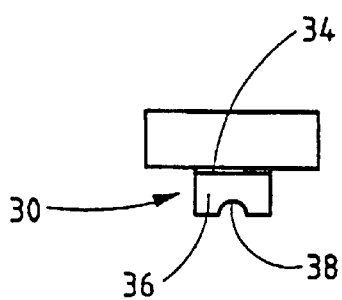
FIG. 5 is an end view of the pressure sensor.

The differential pressure sensor 30, as can be seen more clearly in FIG. 4, comprises a package 32 for processing electrical signals and for connection purposes, and a sensitive surface 34 made of piezoelectric material. A block 36 made of gel is provided in register with the sensitive surface 34, the block penetrating in sealed manner into the recess 18 in the body 10. In addition, the block 36 has a surface which defines in part a portion of a cylindrical surface 38 having the same radius as the axial bore, as can be seen in FIGS. 4 and 5. This cylindrical surface portion 38 is flush with the inside wall 16a of the axial bore 16 formed in the body 10.

Naturally the right cross-section of the bore 16 need not be circular. Under such circumstances, the surface 38 of the block 36 should be of a shape that matches said right cross-section.

Because of this disposition, there is no singularity in the axial bore 16 in the vicinity of the pressure sensor. Consequently, this avoids any risk of air accumulating while the liquid is flowing along the tube and thus along the axial bore 16.

It should also be specified that the block 34 is made using a non-compressible gel which transmits in full the pressure it receives on its cylindrical surface 38 to the sensitive piezoelectric surface 34 of the differential pressure sensor.

Naturally, it is possible to use a pressure sensitive converter element other than a piezoelectric membrane. Nevertheless, a block of incompressible material should be interposed between any such sensitive element and the liquid whose pressure is to be measured.

It will be understood that the pressure measurement performed by the pressure sensor 30 corresponds to the pressure that actually obtains in the bore 16, i.e. in the tube carrying the flow of liquid, and this measured pressure corresponds at all times to the actual pressure in the tube. There is no compressible material interposed between the flow of liquid and the sensitive surface of the pressure sensor.

It will thus be understood that the pressure measurement device of the invention exactly solves the problem posed since, because of its shape, it makes it possible to measure the actual pressure of the liquid flowing in the tube 20, 22, and to do so at all times, without any significant time constant appearing in the measurement. It is thus possible, while performing phaco-emulsification, to use the information provided by the pressure sensor to control the liquid extraction pump effectively as a function of pressure, and in particular to control the flow rate of the liquid very accurately on the basis of the pressure measured in the tube even in the event of lens debris clogging the cannula mounted at the end of the upstream tube portion 20, and thus to operate in spite of the risk that the pressure might be subject to sudden variations.

Figure 6:
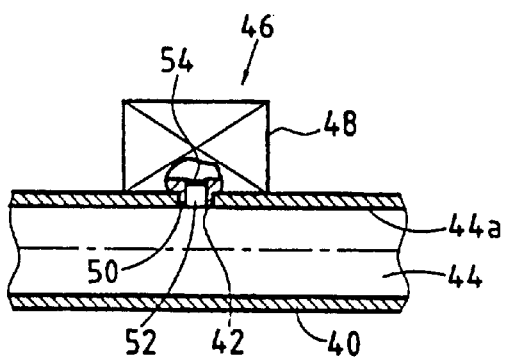
FIG. 6 is a fragmentary axial section through a econd embodiment of the pressure measurement device.

FIG. 6 shows another embodiment of the pressure measurement device. There can be seen the duct means 40 having a radial orifice 42 formed in the wall thereof to open out into the axial bore 44. The inside wall 44a of the bore is substantially cylindrical.

The sensor 46 comprises a body 48 containing the converter element and an extension constituted by a cylindrical skirt 50. The outside diameter of the skirt 50 is equal to the diameter of the orifice 42 to ensure that the sensor 46 is fixed in sealed manner on the duct means 40. At the end of the cylindrical cavity 52 defined by the skirt 48 there is mounted the sensitive surface 54 of the sensor, which surface is subjected to the pressure. This sensitive surface is made of an incompressible material which transmits the pressure of the liquid to the converter element of the sensor.

The cavity 52 is of very small dimensions so that the dead volume it defines relative to the inside wall 44a of the duct means is also very small. In the example described, this volume is of the order of 4 mm$^3$. In any event, steps should be taken to ensure that this dead volume is less than 10 mm$^3$. Thus, even if air does become trapped therein under the effect of the suction, the volume of air is small enough to avoid the risk of introducing significant distortion in the measurement of the pressure of the liquid in the tube.

What is claimed is:

1. A tube assembly comprising:

a duct having an axial bore with a wall having an inside face, an orifice passing through said duct wall and communicating with said bore at said inside face, a first connecting end and a second connecting end, said axial bore of said duct having a substantially constant cross-sectional size and shape along its length;

a first tube having an inside surface forming an axial bore substantially equal in cross-sectional size and shape to the axial bore of said duct, said first tube being connected to said first end of said duct, the inside face of said duct being substantially flush with the inside surface of said first tube;

a second tube having an inside surface forming an axial bore, substantially equal in cross-sectional size and shape to the axial bore of said duct, said second tube being connected to said second end of said duct the inside face of said duct being substantially flush with the inside surface of said second tube; and a pressure sensor for measuring a pressure of a fluid within said duct, said sensor having a sensitive surface which is subjected to a pressure exerted by a fluid within said duct, said sensitive surface communicating with said orifice, a volume defined by the sensitive surface and an inside surface of said orifice being less than about 10 mm$^3$.

2. The tube assembly according to claim 1 wherein said pressure sensor comprises a body external to the duct and an extension in the form of a cylindrical skirt suitable for cooperating in a sealed manner with said orifice, the pressure sensitive surface being disposed at an inside end of the skirt, the skirt having an axial length that is substantially equal to a thickness of the wall of the duct.

3. The tube assembly according to claim 1, wherein the tube assembly is disposable.

4. The tube assembly according to claim 1, wherein pressures measured by said pressure sensor are negative with respect to atmospheric pressure.

5. A tube assembly comprising:
- a duct having an axial bore with a wall having an inside face, an orifice passing through said duct wall and communicating with said bore at said inside face, a first connecting end and a second connecting end, said axial bore of said duct having a substantially constant cross-sectional size and shape along its length;
- a first tube having a first end, a second end and an inside surface, said second end of said first tube being connected in a sealed manner to said first end of said duct, said inside surface of said first tube being substantially flush with said inside face of said duct;
- a second tube having a first end, an inside surface and a second end, said first end of said second tube being connected in a sealed manner to said second end of said duct, said inside surface of said second tube being substantially flush with said inside face of said duct;
- a cannula connected to said first end of said first tube;
- an extractor pump connected to said second tube at said second end; and
- a pressure sensor for measuring a pressure of a fluid within said duct, said sensor including a sensitive surface which is subjected to a pressure of a fluid in said duct, said sensitive surface being substantially flush over its entire surface with said inside face of said wall of said duct.

6. The tube assembly according to claim 5 wherein said pressure sensitive surface is formed of an incompressible material suitable for transmitting pressure which is applied to said sensitive surface to a converter element of the sensor.

7. The tube assembly according to claim 5 wherein said inside face of said axial bore has a substantially curved configuration and wherein said sensitive surface is curved to conform to the curved configuration of said inside face of said axial bore.

8. The tube assembly according to claim 7, wherein said sensitive surface is semi-circular in cross-sectional shape.

9. The tube assembly according to claim 6, wherein a fluid pressure within said duct is negative with respect to atmospheric pressure.

10. The tube assembly according to claim 6, wherein said tube assembly is disposable.

11. The tube assembly according to claim 6, wherein said duct is formed of a biocompatible, rigid material.

12. The tube assembly according to claim 6 wherein said first and said second tubes each have an interior axial bore defined by said inside surfaces which is substantially equal in cross-sectional size and shape to the cross-sectional size and shape of said axial bore of said duct.

* * * * *